United States Patent [19]
Goddard

[11] Patent Number: 5,811,579
[45] Date of Patent: Sep. 22, 1998

[54] METHOD OF SYNTHESIZING A 2-SUBSTITUTED NITROGEN-CONTAINING COMPOUND

[75] Inventor: John DeMita Goddard, Pinner, United Kingdom

[73] Assignee: Eastman Kodak Company, Rochester, N.Y.

[21] Appl. No.: 836,662

[22] PCT Filed: Nov. 17, 1995

[86] PCT No.: PCT/EP95/04522

§ 371 Date: May 7, 1997

§ 102(e) Date: May 7, 1997

[87] PCT Pub. No.: WO95/29465

PCT Pub. Date: Nov. 2, 1995

[30] Foreign Application Priority Data

Nov. 21, 1994 [GB] United Kingdom ............ 9423458

[51] Int. Cl.⁶ .................................................. C07C 273/00
[52] U.S. Cl. ........................... 564/45; 548/221; 558/232; 558/239; 558/241; 558/252; 558/262; 558/272; 560/142; 564/300
[58] Field of Search ............................. 558/239, 241, 558/252, 272, 232; 560/142; 564/300, 45

[56] References Cited

U.S. PATENT DOCUMENTS 3,567,776  3/1971  Krenzer .................. 560/142

*Primary Examiner*—Michael L. Shippen
*Attorney, Agent, or Firm*—Arthur E. Kluegel

[57] ABSTRACT

The present invention relates to a method of synthesizing a 2-substituted nitrogen containing compound having a formula (I):

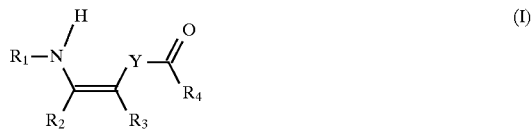

by reacting a hydroxylamine of formula (II);

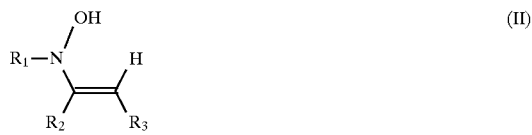

or a nitrone of formula (III):

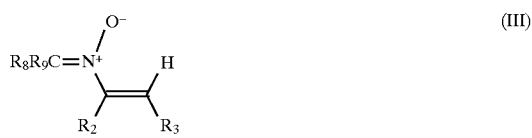

with a compound of formula (IV);

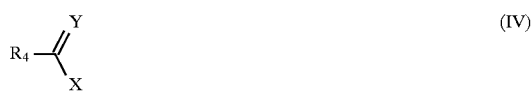

thereby to form an intermediate compound, and thereafter causing or allowing said intermediate compound to undergo a pericyclic sigmatropic rearrangement reaction to form the compound (I); wherein X is a nucleofugal group, Y is selected from $O, S, NH, NR_5$ and $CR_6R_7$, $R_1$ is a group which directs the reactivity of compound (II) on to the oxygen atom and $R_2$ to $R_9$ are each a substituted or unsubstituted aliphatic, aromatic, heteroaryl or cyclic group or hydrogen which is substantially inert or is protected during the reaction.

16 Claims, No Drawings

METHOD OF SYNTHESIZING A 2-SUBSTITUTED NITROGEN-CONTAINING COMPOUND

FIELD OF THE INVENTION

The present invention relates to a method of synthesizing a 2-substituted nitrogen-containing compound and has particular reference to a method of synthesizing an ortho-substituted aryl compound having a nitrogen-containing group in the 1-position. In one aspect, the present invention comprehends a method of producing an aromatic nitrogen-containing compound having a sulphur-containing moiety in the 2-position.

BACKGROUND OF THE INVENTION

Aromatic sulfur-containing compounds are of great importance in the manufacture of photographic, pharmaceutical and pesticidal materials. For example, in photography, aromatic thiols have been found useful as coupling-off groups when incorporated into couplers. It has been found that 2-acylaminothiols are particularly useful as coupling-off groups in magenta couplers, since they exhibit substantially no leuco-dye problem. Aromatic disulfides are of use as intermediates in coupler synthesis and as light stabilizers for magenta dyes.

EP-A-0 251552 discloses a process for producing aminothiophenols and their derivatives comprising the pyrolytic rearrangement of O-(N-acylaminoaryl)-N,N-di(organo) thiocarbamate. This type of rearrangement reaction is known as the Newman-Kwart rearrangement reaction and is described in J. Org. Chem., 31, 410 (1966) by Messrs. Kwart and Evans and in Org. Synth., 51, 139 (1971) by Messrs. Newman and Hetzel. It is thought that the Newman-Kwart rearrangement reaction proceeds via an unstable 4-member ring intermediate.

PROBLEM TO BE SOLVED BY THE INVENTION

The problem with the use of the Newman-Kwart rearrangement reaction to produce aromatic sulfur containing compounds is that high temperatures are required; this makes the process undesirable for synthesis on an industrial scale. EP-A-0 251552 in Example 8, for example, discloses that the pyrolytic rearrangement of O-(N-acetyl-para-aminophenyl)dimethylthiocarbamate is conducted at 280° C. under nitrogen for 2 hours in sulfolane. The present invention seeks to provide a method for producing e.g. aromatic sulfur-containing compounds at lower temperatures, which is thus more susceptible of industrial application as compared with the Newman-Kwart rearrangement reaction referred to above.

SUMMARY OF THE INVENTION

According to one aspect of the present invention therefore there is provided a method of synthesizing a compound having a general formula (I) as follows:

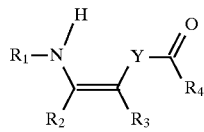

comprising the step of reacting a hydroxylamine of general formula (II):

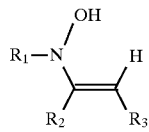

or a nitrone of general formula (III):

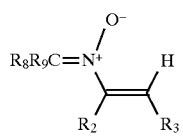

with a compound of general formula (IV):

thereby to form an intermediate compound, and thereafter causing or allowing said intermediate compound to undergo a pericyclic sigmatropic rearrangement reaction to form the compound (I); wherein X is a nucleofugal group, Y is selected from $O, S, NH, NR_5$ and $CR_6R_7$, $R_1$ is a group which directs the reactivity of compound (II) onto the oxygen atom and $R_2$ to $R_9$ are each a substituted or unsubstituted aliphatic, aromatic, heteroaryl or cyclic group or hydrogen which is substantially inert or protected during the reaction.

Said compound (I) may be isolatable; alternatively, in some embodiments, the compound (I) may itself be an intermediate which cannot be isolated. Without wishing to be bound by theory, it is thought that compounds (II) or (III) and (IV) react to form said intermediate compound which is caused or allowed to undergo a pericyclic sigmatropic rearrangement reaction via a pericyclic transition state (V):

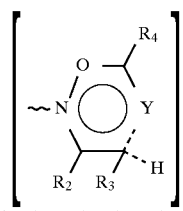

It is thought that the nitrogen-oxygen bond in the intermediate compound breaks as the carbon-Y bond forms accompanied by the elimination of a proton.

In a particular aspect of the present invention, Y may be sulfur, in which case it will be seen that the method of the present invention results in a 2-(sulfur containing group) substituted nitrogen-containing compound.

ADVANTAGEOUS EFFECTS OF THE INVENTION

In some embodiments, the rearrangement of said intermediate compound may proceed at temperatures significantly lower than required for the Newman-Kwart reaction utilised by EP-A-0 251552. The synthesis of the present invention may be carried out at a temperature of 0°–200° C.; in some embodiments the rearrangement may proceed at temperatures in the range 0°–40° C. Typically, the pericyclic sigmatropic rearrangement of the present invention may proceed at about room temperature.

The synthesis according to the present invention, when using a hydroxylamine (II) as a starting material, may be carried out in the presence of base. Said base may be an inorganic or organic base. In some embodiments, the base may be an alkali metal hydride, hydroxide or carbonate, conveniently sodium hydride. Alternatively, an organic base, e.g. a trialkylamine, arylalkylamine or conveniently pyridine or a substituted pyridine such as lutidine, may be employed. The base may be used in an equimolar amount with the hydroxylamine (II).

When the nitrone (III) is the starting material the reaction may be carried out in the absence or presence of a base as hereinabove described.

In one aspect of the invention, when the hydroxylamine (II) is the starting material, $R_1$ may be a group adapted to direct the reaction onto the juxtaposed O atom such as, for example, a group of the formula $R_{10}CO$ wherein $R_{10}$ is hydrogen or a substituted or unsubstituted alkyl, aryl, heteroaryl or cyclic group, especially an acyl or aroyl group; typically $R_1$ may be acetyl or benzoyl. Alternatively when the starting material is the nitrone (III), $R_1$ is the group $R_8R_9C=$, wherein $R_8$ and $R_9$ are as hereindefined.

As used herein and throughout the specification the term substituted includes substitution with one or more of the following:—halogen, alkyl, aryl, heteroaryl, carboxylic acid, alkoxycarbonyl, aryloxycarbonyl, primary or secondary alkyl- or aryl-amido, alkyl- or aryl-sulfonamido, primary, secondary or tertiary amino, nitro, alkoxy, aryloxy, acyloxy, alkyl- or aryl-carbamoyl, alkyl- or aryl-sulfamoyl, alkyl- or aryl-sulfonyl and alkyl- or aryl-sulfonyloxy.

$R_2$, $R_3$, $R_4$, $R_5$, $R_6$, $R_7$, $R_8$ and $R_9$ independently may be hydrogen or a substituted or unsubstituted alkyl, aryl heteroaryl or cyclic group. In some embodiments, $R_2$ and $R_3$, together with the linking carbon atoms, may form a substituted or unsubstituted unitary aryl group, or a 3–8 membered heterocyclic ring which may contain one or more further heteroatoms selected from N, O and S, said heterocyclic ring being unsubstituted or substituted. In a particular aspect of the invention, $R_2$ and $R_3$ may form a substituted or unsubstituted phenyl group.

In preferred embodiments, X may be a halide nucleofugal group, preferably chloride. Y is preferably O or most preferably S.

In addition to the above and as a preferred embodiment $R_4$ may be a group, $NR_{11}R_{12}$, wherein $R_{11}$ and $R_{12}$ are each hydrogen or a substituted or unsubstituted alkyl or aryl group; typically $R_4$ may be $NMe_2$. Alternatively $R_4$ may be a substituted or unsubstituted alkoxy, aryloxy, heteroaryloxy or cyclic-oxy group, typically ethoxy or phenoxy. Thus in a particular aspect of the present invention, compound (IV) may be dimethylthiocarbamoyl chloride, wherein Y=S and $R_4=NMe_2$, which is commercially available e.g. from Messrs. Aldrich under the reference 13,589-5 (1992–1993 Catalogue, page 541). Alternatively, compound (IV) may be a chloroformate of formula (VI):

in which $R_{13}$ is a substituted or unsubstituted alkyl, aryl, heteroaryl or cyclic group, typically ethyl or phenyl.

Where Y=S the sigmatropic rearrangement may proceed at 0°–40° C. or room temperature. Where Y=O, heat may be required in some embodiments for the sigmatropic rearrangement of the intermediate to proceed; typically the rearrangement may be conducted at 75°–200° C., e.g. 150° C. In such case the intermediate compound may be isolated, redissolved (if necessary) and refluxed. Alternatively the intermediate compound may be heated in the reaction mixture without being isolated. Where the intermediate compound is liquid it may be isolated and heated directly, e.g. in an oil bath.

Where a chloroformate (IV) is used the method of the present invention may lead to a 2-(oxygen-containing group) substituted nitrogen containing compound.

In a particular aspect of the present invention, hydroxylamine (II) or nitrone (III) may respectively be:

wherein $R_{14}$ is hydrogen or a substituent as included in the term substituted as hereinabove defined; typically, said hydroxylamine (II) may be:

Where compound (VII) is reacted with a thioacyl chloride, $R_4CSX$, in accordance with the method of the present invention, compound (I) may be of formula (X):

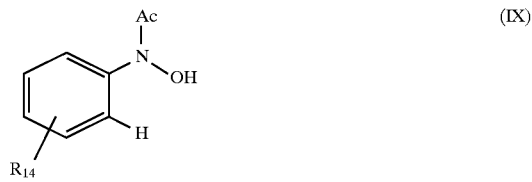

Compound (X) may be isolated or alternatively, in some embodiments, may be caused or allowed to undergo rearrangement and oxidation to form a disulfide of formula (XI) as follows:

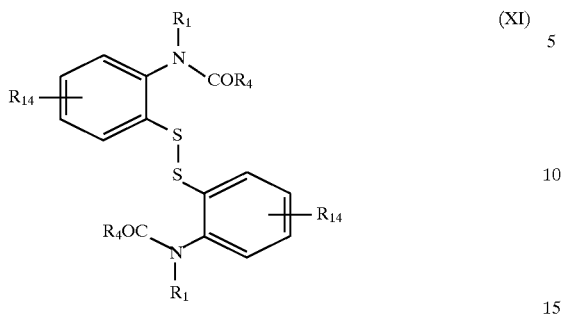

Said rearrangement and oxidation of compound (X) may be carried out in the presence of base as hereinbefore described and an oxidising agent.

In some embodiments when Y=S excess base may be added to a reaction mixture containing hydroxylamine (II) and compound (IV) so that the reaction proceeds straight to a disulfide-containing compound. In particular when excess base is added to a reaction mixture of hydroxylamine (VII) and compound (IV) the reaction proceeds directly to compound (XI). Typically the rearrangement and oxidation may be carried out in the presence of air to provide the oxidising conditions required.

Where compound (VII) is reacted with a chloroformate (VI) in accordance with the present invention, compound (I) may have the formula (XII) as follows:

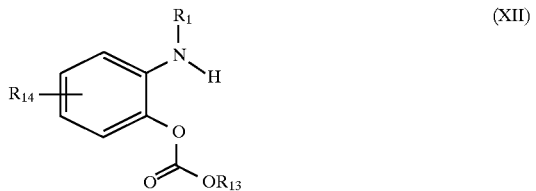

In some embodiments, e.g. where $R_1$ is acetyl and $R_{13}$ is ethyl, compound (XII) may be isolatable.

Alternatively, e.g. where $R_1$ is acetyl and $R_{13}$ is phenyl, compound (XII) may be an intermediate compound which cannot be isolated. Compound (XII) may be caused or allowed to undergo further rearrangement to form a heterocyclic compound of formula (XIII) as follows:

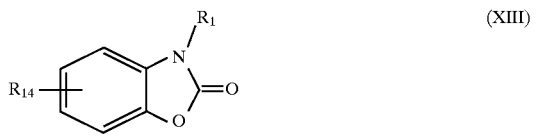

DETAILED DESCRIPTION OF THE INVENTION

Following is a description by way of example only of methods of carrying the present invention into effect.

EXAMPLE 1

The following sequence has been carried out:

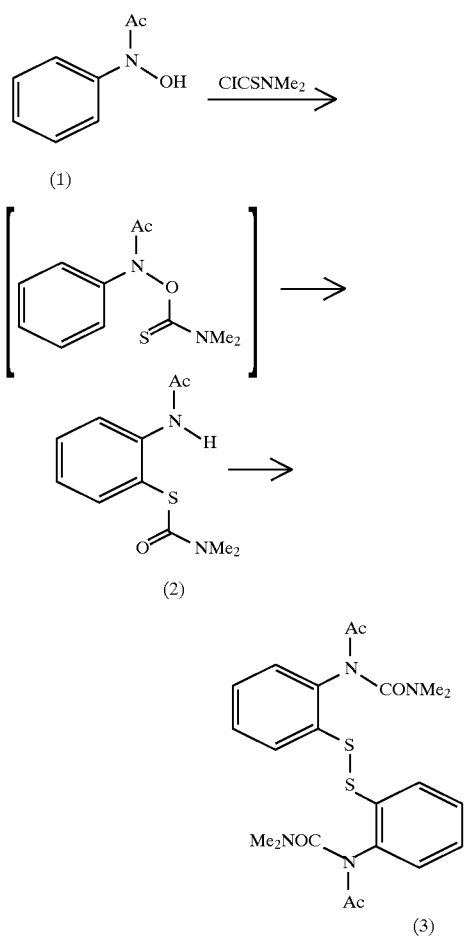

N-Acetyl-N-phenylhydroxylamine (1) was prepared by a literature method (Oxley, Adger, Sasse and Forth, *Organic Synthesis*, 1989, 67, 187).

Preparation of Compound (2)

Sodium hydride (60% in oil) (1.2 g, 0.03 mole) was washed with dry THF under nitrogen in order to remove the oil. Dry dimethylformamide (120 ml) was added and the mixture was cooled in an ice bath with stirring. Freshly prepared N-acetyl-N-phenylhydroxylamine (1) (4.53 g, 0.03 mole) was added portionwise to the suspension whereupon a white precipitate was formed. The suspension was stirred at 10° C. for 30 minutes and then dimethylthiocarbamoyl chloride (3.7 g, 0.03 mole) was added portionwise. The mixture was allowed to warm to room temperature. Ethyl acetate (1 liter) was added to the reaction mixture and the solution extracted with dilute hydrochloric acid (200 ml). The organic layer was washed with several portions of water and then dried (MgSO$_4$). The solvent was removed under vacuum to yield a brown oil, probably containing some dimethylformamide. The product was dissolved up in a mixture of cyclohexane and diethyl ether and decanted off a brown residue. Slow evaporation of the solvent under vacuum induced crystallisation. The product was filtered off as pale buff coloured crystals (4.7 g, 65%); m.p.127° C.–128° C.

Preparation of Compound (3)

If the above reaction is repeated using a 15% excess of sodium hydride and in the presence of air, disulfide (3) is obtained in similar yields to compound (2); m.p. 171° C.

EXAMPLE 2

Preparation of Compound 4

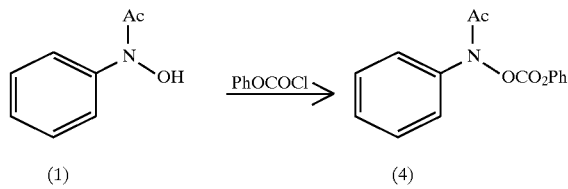

N-Acetyl-N-phenylhydroxylamine (1) (6.0 g, 0.04 mole) was dissolved in a mixture of dry dichloromethane (150 ml) and dry pyridine (20 ml). Phenyl chloroformate (6.4 g, 0.04 mole) was added dropwise with stirring and the mixture allowed to stand overnight.

Dichloromethane (300 ml) was added to the mixture which was then washed with 0.1M hydrochloric acid until the washings remained acidic. The solution was dried over magnesium sulphate, filtered and then evaporated to dryness under reduced pressure. The product (4) was obtained as a pale yellow oil (10.2 g, 94%). The product (4) was one spot on a silica tlc plate when eluted with 1:1 petrol (60°–80° C.)/ethyl acetate and also had mass and nmr spectra which were consistent with the proposed structure.

Preparation of Compound (5)

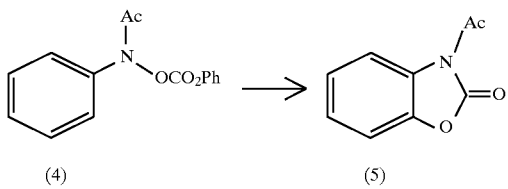

Compound (4) (10.2 g, 0.0376 mole) was dissolved in toluene (150 ml) and heated to reflux for 5 hours. The solvent was evaporated to dryness and the residue recrystallized from diethyl ether. The product (5) was obtained as cream coloured plates (4.7 g, 70%). The product (5) had mass and nmr spectra which were consistent with the proposed structure and was identical to a sample prepared by an independent route.

EXAMPLE 3

Preparation of Compound 6

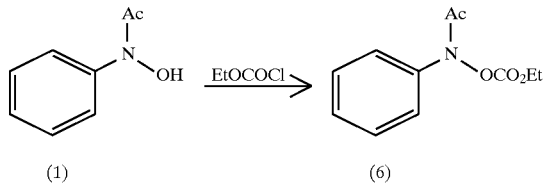

N-Acetyl-N-phenylhydroxylamine (1) (3.02 g, 0.02 mole) was dissolved in a mixture of dry dichloromethane (100 ml) and pyridine (10 ml). Ethyl chloroformate (2.2 g, 0.02 mole) was added dropwise. The solution was stirred for 1.5 hours and a white precipitate was noted. Dichloromethane (800 ml) was added to the reaction mixture which was then washed with 0.1M hydrochloric acid until the washings remained acidic. The solvent was dried over magnesium sulphate and then removed on the rotary evaporator under reduced pressure. A quantitative yield (4.5 g) of the product (6) was obtained as a pale yellow oil. The product (6) had mass and nmr spectra which were consistent with the proposed structure.

Preparation of Compound 7

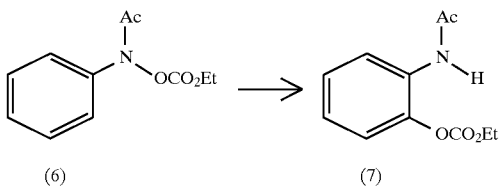

Compound (6) (4.5 g, 0.02 mole) was heated in an oil bath to 150° C. for 1 hour. The oily product (7) looked reasonably pure by tlc on silica using an eluant of 1:1 petrol (60°–80° C.)/ethyl acetate. Also, the product (7) had nmr and mass spectra which were consistent with the proposed structure. The yield was quantitative.

I claim:

1. A method of synthesizing a compound, comprising: reacting a hydroxylamine of the general formula (II):

with a compound of general formula (IV):

to form the compound (I)

wherein
X is a nucleofugal group;
Y is S;
$R_1$ is the group $R_{10}CO$— in which $R_{10}$ is an alkyl, aryl, or heteroaryl group;
$R_2$, $R_3$, and $R_5$ to $R_9$ are each a substituted or unsubstituted aliphatic or cyclic group or hydrogen which is inert or protected during the reaction; and
$R_4$ is selected from the groups suitable for $R_2$ and from substituted or unsubstituted amino, alkoxy, aryloxy and heteroaryloxy groups;
provided that $R_2$ and $R_3$ may join to form a ring.

2. A method as claimed in claim 1 wherein $R_2$ and $R_3$, together with the linking carbon atoms, form a substituted or unsubstituted unitary aryl group.

3. A method as claimed in claim 2 wherein the aryl group is a phenyl group.

4. A method as claimed in claim 1 wherein X is a halide group.

5. A method as claimed in claim 1 where $R_4$ is an amino group $NR_{11}$, $NR_{12}$, wherein $R_{11}$ and $R_{12}$ are each hydrogen or a substituted or unsubstituted alkyl or aryl group.

6. A method as claimed in claim 5 wherein $R_4$ is dimethylamino.

7. A method as claimed in claim 6 wherein the compound of formula (IV) is dimethylaminothiocarbamoyl chloride.

8. A method as claimed in claim 1 wherein $R_4$ is a substituted or unsubstituted alkoxy, aryloxy, or heteroaryloxy group.

9. A method as claimed in claim 1 wherein the compound of formula (I) has the formula (X):

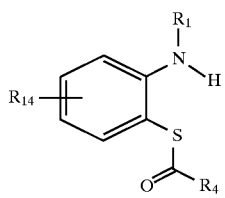
(X)

wherein $R_{14}$ is H or a substituent.

10. A method as claimed in any one of the preceding claims, wherein said sigmatropic rearrangement is conducted at a temperature of 0°–200° C.

11. A method as claimed in claim 1 in which the reaction is conducted at a temperature of 0°–40° C.

12. A method as claimed in claim 1 wherein the reaction between compound (II) and compound (IV) is carried out in the presence of an organic or inorganic base.

13. A method as claimed in claim 12 wherein the base is sodium hydride, pyridine or lutidine.

14. A method as claimed in claim 12 wherein the reaction between compound (II) and compound (IV) is carried out in the presence of equimolar amounts of base and compound of formula (II).

15. A method as claimed in claim 1 wherein said hydroxylamine (II) has the formula (VII) as follows:

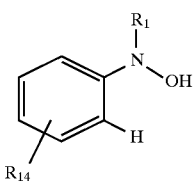
(VII)

wherein $R_{14}$ is a substituted or unsubstituted alkyl or aryl group or hydrogen.

16. A method as claimed in claim 1 wherein the compound of formula (I) has formula (X):

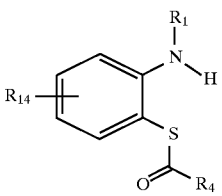
(X)

wherein $R_{14}$ is a substituted or unsubstituted alkyl or aryl group or hydrogen, comprising the additional subsequent step of oxidizing compound (X) to yield a disulfide compound of formula (XI):

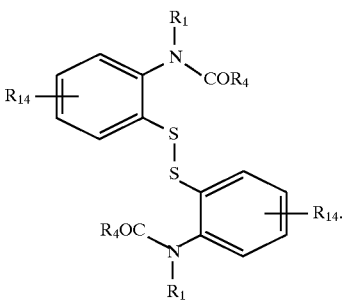

* * * * *